United States Patent
Yale et al.

[11] 3,933,836
[45] Jan. 20, 1976

[54] PYRIDINYLIDENE GUANIDINES

[75] Inventors: Harry L. Yale, New Brunswick; James Arthur Bristol, Mercerville, both of N.J.

[73] Assignee: E. R. Squibb & Sons, Inc., Princeton, N.J.

[22] Filed: Sept. 26, 1974

[21] Appl. No.: 509,513

[52] U.S. Cl. ........ 260/296 R; 260/294.8 F; 424/263
[51] Int. Cl.² .............. C07D 213/06; C07D 213/26
[58] Field of Search .................. 260/296 R, 294.8 F

[56] References Cited
UNITED STATES PATENTS

| | | | |
|---|---|---|---|
| 3,040,050 | 6/1962 | Biel ............................ | 260/296 R |
| 3,352,878 | 11/1967 | Minor ........................... | 260/296 R |

*Primary Examiner*—Henry R. Jiles
*Assistant Examiner*—Bernard I. Dentz
*Attorney, Agent, or Firm*—Lawrence S. Levinson; Merle J. Smith; Donald J. Barrack

[57] ABSTRACT

Compounds having the structure

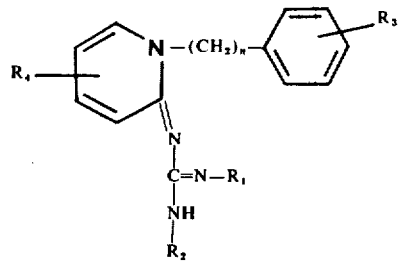

and the pharmaceutically acceptable salts thereof, wherein $R_1$ and $R_2$ are the same or different and are selected from alkyl, cycloalkyl, aryl and arylalkyl; $R_3$ is hydrogen, halogen, trifluoromethyl, alkoxy, aryloxy, or dialkylamidosulfonyl; $R_4$ is hydrogen, halogen, alkyl, alkoxy or aryl; and $n$ is 1 or 2, are useful central nervous system stimulants.

14 Claims, No Drawings

PYRIDINYLIDENE GUANIDINES

BRIEF DESCRIPTION OF THE INVENTION

Guanidines having the structure

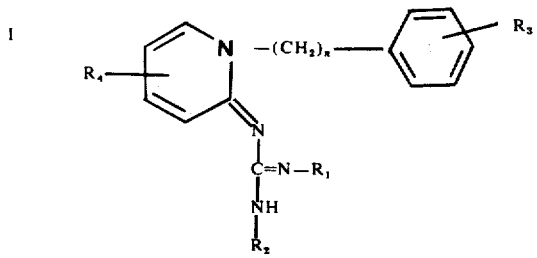

I and the pharmaceutically acceptable salts thereof, are useful as central nervous system stimulants. In formula I, and throughout the specification, the symbols are as defined below:

$R_1$ and $R_2$ are the same or different and can be alkyl, cycloalkyl, aryl or arylalkyl;

$R_3$ can be hydrogen, halogen, trifluoromethyl, alkoxy, aryloxy or dialkylamidosulfonyl;

$R_4$ can be hydrogen, halogen, alkyl, alkoxy or aryl; and $n$ can be 1 or 2.

The term "alkyl" as used throughout the specification, refers to alkyl groups having 1 to 6 carbon atoms. Alkyl groups having 1 to 3 carbon atoms are preferred.

The term "cycloalkyl", as used throughout the specification, refers to cycloalkyl groups having 3 to 6 carbon atoms, i.e., cyclopropyl, cyclobutyl, cyclopentyl and cyclohexyl.

The term "aryl", as used throughout the specification, refers to phenyl or phenyl substituted with 1 or 2 groups selected from alkyl, alkoxy, halogen and trifluoromethyl.

The term "halogen", as used throughout the specification, refers to chlorine, bromine, fluorine and iodine; chlorine and bromine are the preferred halogens.

The term "alkoxy", as used throughout the specification, refers to a group having the formula Y—O— wherein Y is alkyl as defined above. Alkoxy groups having 1 to 3 carbon atoms are preferred.

The term "aryloxy", as used throughout the specification, refers to a group having the formula Z—O— wherein Z is aryl as defined above.

DETAILED DESCRIPTION OF THE INVENTION

The compounds of formula I, and the pharmaceutically acceptable salts thereof, are central nervous system stimulants and are useful for relieving depression (particularly endogenous depression) in mammals, in a manner similar to imipramine, when administered in a daily dose of from 0.5 mg/kg to 3 mg/kg, preferably 1 mg/kg to 2 mg/kg.

The compounds of the present invention can be administered orally in the form of tablets, troches, capsules, elixirs, suspensions, syrups, wafers, chewing gum and the like. Such compositions and preparations should contain at least 0.1% of active compound. The percentage of active compound in the compositions and preparation can, of course, be varied and can conveniently be between about 5% and about 75% or more of the weight of the unit. Preferred compositions according to the present invention are prepared so that an oral dosage unit form contains between about 5 and 200 milligrams of active compounds.

The compounds of the present invention can be prepared from pyridinimines having the structure

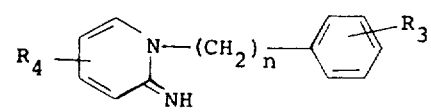

II and the carbodiimides having the structure $$R_1-N=C=N-R_2$$

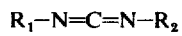

The pyridinimines of formula II and the carbodiimides of formula III can be reacted in an organic solvent, e.g., an alkanol such as t-butanol, at a temperature of from about 20°C to 100°C, preferably at the reflux temperature of the solvent, for a period of from about 3 hours to 4 days.

The pyridinimines of formula II where $n$ is 2 are known; see for example, U.S. Pat. No. 3,825,549 to Yale et al. and Yale et al., Journal of Heterocyclic Chemistry, 11:331 (1974).

The pyridinimines of formula II where $n$ is 1 are novel intermediates, and as such they constitute a part of this invention. They can be prepared by treating a quaternary derivative having the structure

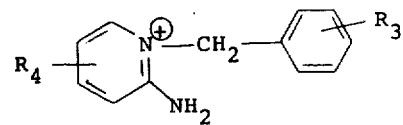

IV wherein X is an anion such as a halogen, with a base such as sodium alkoxide, potassium hydroxide, potassium carbonate, etc. in a solvent such as an alkanol or a mixture of an alkanol and water.

The quaternary derivatives of formula IV can be prepared by reacting an o-aminopyridine of the structure

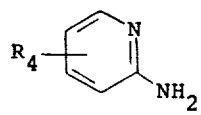

V with a toluene derivative having the structure

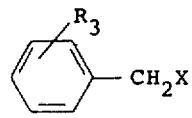

VI

The reaction can be run in an organic solvent, e.g., toluene or xylene, under reflux conditions for about 4 hours to 2 days.

The pyridinylidene quanidines of formula I can be converted to their pharmaceutically acceptable acid-addition salts using procedures well known in the art. Illustrative of the salts contemplated for use in this invention are the hydrohalides (e.g., the hydrochloride and hydrobromide), sulfate, nitrate, tartrate, phosphate, maleate, fumarate, citrate, succinate, methanesulfonate, benzenesulfonate, toluenesulfonate and the like.

Those compounds of formula I wherein $R_1$ and $R_2$ are different can exist as a tautomeric mixture wherein the tautomers having the structures 0.036 mole) in 100 ml t-butanol is heated at reflux for 24 hours. The solution is cooled and concentrated in vacuo to give a solid. The solid is recrystallized from 200 ml of hexane to give 5.48 g of the title compound which sinters at 132°C and melts at 142.5°–145°C.

EXAMPLE 3

N-[1-[2-(2-Bromophenyl)ethyl]-2(1H)-pyridinylidene]-N′,N″-dicyclohexyl guanidine A solution of 1-[2-(2-bromophenyl)ethyl]-2-iminopyridine (2.77 g, 0.01 mole) and dicyclohexylcarbodiimide (2.06 g, 0.01 mole) in 30 ml of t-butanol is heated at reflux for 21.5 hours under a nitrogen blan-

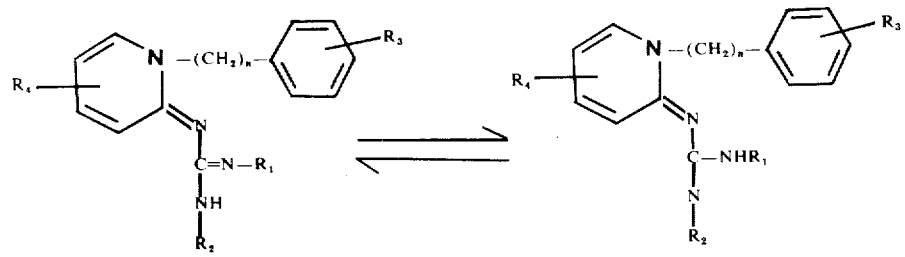

The following examples are specific embodiments of this invention.

EXAMPLE 1

N-[1-[2-(2-Bromophenyl)ethyl]-2(1H)-pyridinylidene]-N′,N″-bis(1-methylethyl)guanidine A solution of 1-[2-(2-bromophenyl)ethyl]-2-iminopyridine (2.77 g, 0.01 mole) and diisopropylcarbodiimide (1.05 g, 0.012 mole) in 30 ml of t-butanol is heated at reflux in a nitrogen atmosphere for 24 hours. The solution is cooled to room temperature and concentrated in vacuo to give a solid. This is recrystallized from 50 ml of hexane to yield a semi-solid, after cooling to −30°C. Recrystallization of this material from 70 ml of hexane yields 1.83 g of the title compound which sinters at 119°C and melts at 125°–128°C.

EXAMPLE 2

N,N″-Dicyclohexyl-N′-[1-(2-phenylethyl)-2(1H)-pyridinylidene]guanidine

A solution of 1-(2-phenylethyl)-2-iminopyridine (5.9 g, 0.030 mole) and dicyclohexylcarbodiimide (7.26 g, ket. The solution is cooled to room temperature and diluted with 60 ml of hexane. The diluted solution is cooled and scratched in a dry ice bath to induce crystallization. The mixture is allowed to warm to room temperature and is filtered to give 0.58 g of material which sinters at 121°C and melts at 125°–129°C. The filtrate is concentrated in vacuo and the residual oil is cooled in an ice bath and scratched under 40 ml of hexane to give 1.32 g of material which sinters at 100°C and melts at 108°–110°C. The two batches of material are combined and dissolved in a boiling solution of 60 ml of cyclohexane and 60 ml hexane and filtered. The solution is cooled for several hours at −30°C, filtered and washed with cooled hexane to yield 1.33 g of the title compound, melting point 127°–129.5°C.

EXAMPLES 4–6

Following the procedure of Example 1 but substituting the compound shown in column I for 1-[2-(2-bromophenyl)ethyl]-2-iminopyridine, and the compound shown in column II for diisopropylcarbodiimide, the compound shown in column III is obtained.

| Example | Column I | Column II | Column III |
|---|---|---|---|

| Example | Column I | Column II | Column III |
|---|---|---|---|
| 5 | 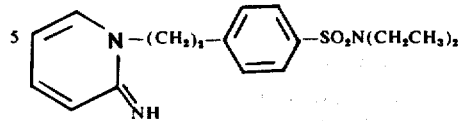 | 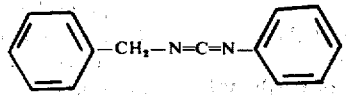 | 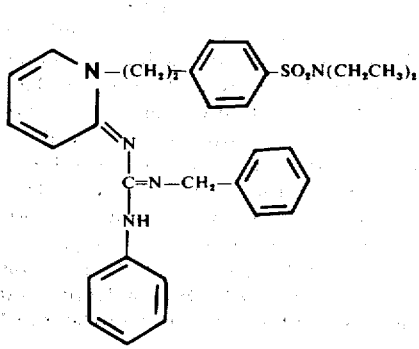 |
| 6 | 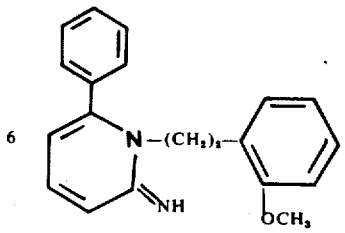 | 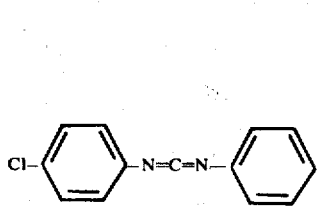 | 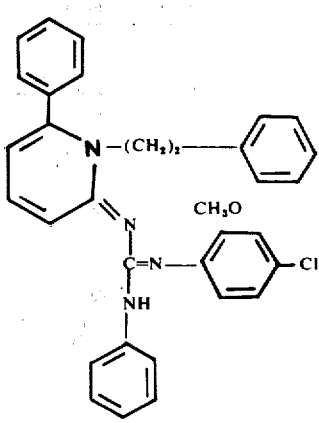 |

EXAMPLE 7

N,N''-Dicyclohexyl-N'-[1-(phenylmethyl)-2(1H)pyridinylidene]guanidine

A. 2-Amino-1-(phenylmethyl)pyridinium bromide

A solution of α-bromotoluene (100.0 g), 2-aminopyridine (82.0 g) and 1000 ml of xylene are heated under reflux for 7 hours to give 99.1 g of the title compound, melting point 187°–190°C.

B. 1-(Phenylmethyl)-2(1H)-pyridinimine

To a solution of 2-amino-1-(phenylmethyl)-pyridinium bromide (94.5 g) in 700 ml of methanol is added, portionwise, a total of 38.5 g of sodium methoxide. The mixture is stirred and heated under reflux conditions for 2.5 hours. Workup yields 63.4 g of the title compound, melting point 52°–54°C.

C. N,N''-Dicyclohexyl-N'-[1-(phenylmethyl)-2(1H)pyridinylidene]guanidine

A solution of 1-(phenylmethyl)-2(1H)-pyridinimine (5.51 g) and dicyclohexylcarbodiimide (7.26 g) in 100 ml of t-butanol is heated under reflux conditions for 23 hours and concentrated in vacuo. The residual solid is recrystallized from petroleum ether to give 6.3 g of the title compound, melting point 111°–115°C.

EXAMPLE 8

1-[[4-(N,N-Dimethylamidosulfonyl)phenylmethyl]-2(1H)-6-methoxypyridinylidene]-N'-cyclohexyl-N''-phenylguanidine A. Methyl 4-(N,N-Dimethylamidosulfonyl)benzoate To a solution of methyl 4-aminobenzoate (151.0 g) in 400 ml of 2.5 N hydrochloric acid is added, dropwise, a solution of sodium nitrite (79.0 g) in 200 ml of water. The mixture is stirred at 0°C for 15 minutes and then treated for 2 hours with a stream of gaseous sulfur dioxide. The oil that separates from the aqueous phase is dissolved in 350 ml of ether and the solution is washed with aqueous saturated sodium chloride, dried and added to 500 ml of 2.5 N ethanolic dimethylamine which has been cooled to 0°C. The mixture is allowed to warm to 20°C and then heated under reflux for 1 hour. Concentration of the mixture yields the title compound.

B. 4-(N,N-Dimethylamidosulfonyl)benzyl alcohol

To a suspension of lithium aluminum hydride (19.0 g) and 500 ml of tetrahydrofuran is added a solution of methyl 4-(N,N-dimethylamidosulfonyl)benzoate (121.5 g) in 200 ml tetrahydrofuran, dropwise with stirring. The mixture is heated under reflux for 2 hours. Workup yields the title compound.

C. 4-(N,N-Dimethylamidosulfonyl)benzyl chloride 4-(N,N-Dimethylamidosulfonyl)benzyl alcohol (54.0 g), anhydrous benzene (250 ml) and phosphorous trichloride (40.0 g) are heated under reflux for 2 hours, cooled and poured on crushed ice. Ether extraction yields the title compound in the form of an oil which is purified by distillation in vacuo.

D. 2-Amino-1-[4-(N,N-dimethylamidosulfonyl)-phenylmethyl]-6-methoxypyridinium chloride A mixture of 4-(N,N-dimethylamidosulfonyl)benzyl chloride (23.4 g), 2-amino-6-methoxypyridine (12.4 g) and 100 ml of anhydrous xylene are heated under reflux conditions for 24 hours. Workup yields the title compound.

E. 1-[4-N,N-Dimethylamidosulfonyl)phenylmethyl]-6-methoxy-2(1H)-pyridinimine

To a solution of 2-amino-1-[4-(N,N-dimethylamidosulfonyl)phenylmethyl]-6-methoxypyridinium chloride (13.8 g) and 100 ml of methanol is added a solution of sodium methoxide (3.3 g) in 50 ml of methanol, dropwise and with stirring. The mixture is stirred and heated under reflux for 2.5 hours and concentrated to dryness in vacuo. The residue is partitioned between 100 ml each of chloroform and water and the chloroform layer is separated, washed, dried and concentrated to yield the title compound.

F. 1-[[4-(N,N-Dimethylamidosulfonyl)phenylmethyl]2(1H)-6-methoxypyridinylidene]-N'-cyclohexyl-N''-phenylguanidine A solution of 1-[4-N,N-dimethylamidosulfonyl)-phenylmethyl]-6-methoxy-2(1H)-pyridinimine (3.1 g) and phenylcyclohexylcarbodiimide (2.0 g) in 50 ml t-butanol is heated under reflux conditions for 24 hours and concentrated to dryness in vacuo to yield the title compound.

EXAMPLES 9–13

Following the procedure of Example 7, but substituting the compound shown in column I for 2-aminopyridine, the compound shown in column II for α-bromotoluene, and the compound shown in column III for dicyclohexylcarbodiimide, the compound shown in column IV is obtained.

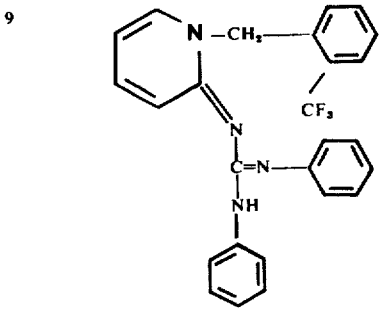

Example Column IV -continued

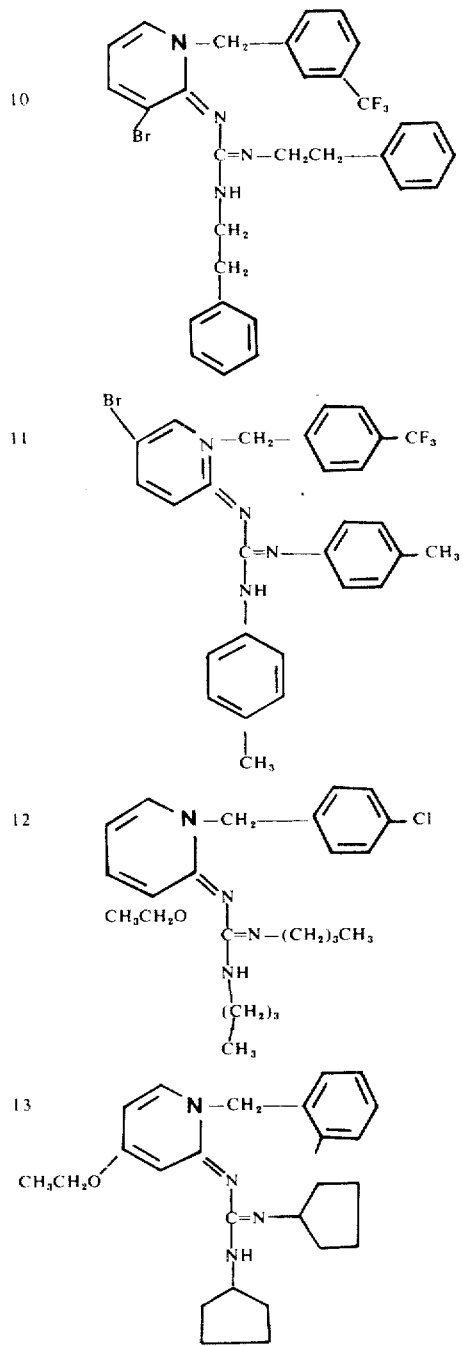

What is claimed is:
1. A compound having the structure

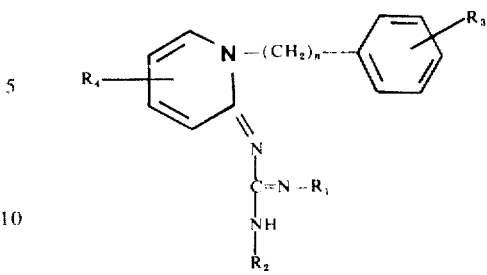

or a pharmaceutically acceptable salt thereof, wherein $R_1$ and $R_2$ are the same or different and are alkyl, cycloalkyl, aryl or arylalkyl; $R_3$ is hydrogen, halogen, trifluoromethyl, alkoxy, aryloxy or dialkylamidosulfonyl; $R_4$ is hydrogen, halogen, alkyl, alkoxy or aryl; and $n$ is 1 or 2; wherein alkyl and alkoxy refer to groups having 1 to 6 carbon atoms; cycloalkyl refers to groups having 3 to 6 carbon atoms; and aryl refers to phenyl or phenyl substituted with 1 or 2 alkyl, alkoxy, halogen or trifluoromethyl groups.

2. A compound in accordance with claim 1 wherein $R_1$ and $R_2$ are the same.

3. A compound in accordance with claim 1 wherein $R_3$ is hydrogen.

4. A compound in accordance with claim 1 wherein $R_3$ is halogen.

5. A compound in accordance with claim 4 wherein $R_3$ is bromine.

6. A compound in accordance with claim 2 wherein $R_1$ and $R_2$ are alkyl.

7. A compound in accordance with claim 2 wherein $R_1$ and $R_2$ are cycloalkyl.

8. A compound in accordance with claim 2 wherein $R_1$ and $R_2$ are aryl.

9. A compound in accordance with claim 2 wherein $R_1$ and $R_2$ are arylalkyl.

10. A compound in accordance with claim 1 wherein $R_4$ is hydrogen.

11. The compound in accordance with claim 1 having the name N-[1-[2-(2-bromophenyl)ethyl]-2(1H)-pyridinylidene]-N',N''-bis-(1-methylethyl)guanidine.

12. The compound in accordance with claim 1 having the name N',N''-dicyclohexyl-N-[1-(2-phenylethyl)-2(1H)-pyridinylidene]guanidine.

13. The compound in accordance with claim 1 having the name N-[1-[2-(2-bromophenyl)ethyl]-2(1H)-pyridinylidene]-N',N''-dicyclohexyl guanidine.

14. The compound in accordance with claim 1 having the name N,N''-dicyclohexyl-N'-[1-(phenylmethyl)-2(1H)-pyridinylidene]guanidine.

* * * * *

UNITED STATES PATENT AND TRADEMARK OFFICE
CERTIFICATE OF CORRECTION

PATENT NO. : 3,933,836
DATED : January 20, 1976
INVENTOR(S) : Harry L. Yale and James A. Bristol It is certified that error appears in the above-identified patent and that said Letters Patent are hereby corrected as shown below:

Column 1, line 66, "preparation" should read
-- preparations --.

Example 6, column III should read:

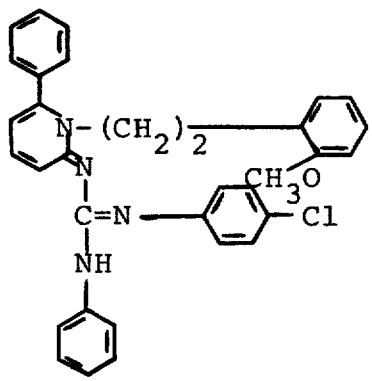

Example 10, Column II, should read:

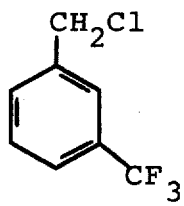

UNITED STATES PATENT AND TRADEMARK OFFICE
CERTIFICATE OF CORRECTION

PATENT NO. : 3,933,836
DATED : January 20, 1976
INVENTOR(S) : Harry L. Yale and James A. Bristol It is certified that error appears in the above-identified patent and that said Letters Patent are hereby corrected as shown below:

Example 9, Column IV should read:

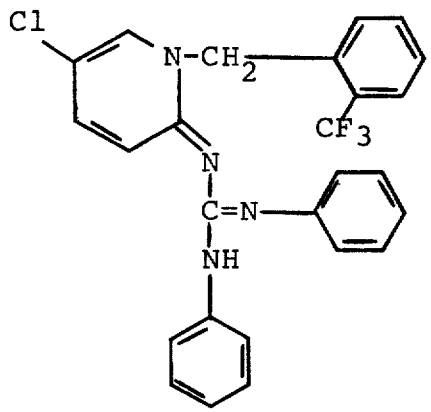

Example 13, Column IV should read:

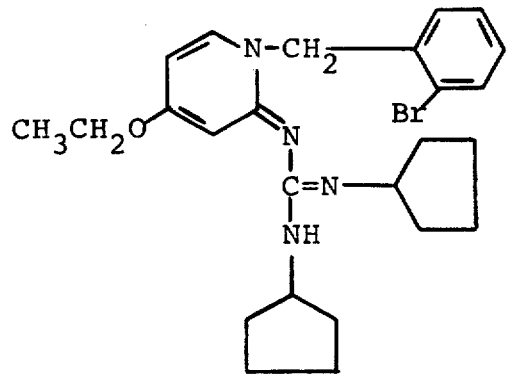

Signed and Sealed this eighteenth Day of May 1976

[SEAL]

Attest:

RUTH C. MASON
*Attesting Officer*

C. MARSHALL DANN
*Commissioner of Patents and Trademarks*